(12) United States Patent
Kuzum et al.

(10) Patent No.: US 10,791,946 B2
(45) Date of Patent: Oct. 6, 2020

(54) TRANSPARENT, FLEXIBLE, LOW-NOISE ELECTRODES FOR SIMULTANEOUS ELECTROPHYSIOLOGY AND NEURO-IMAGING

(71) Applicant: THE TRUSTEES OF THE UNIVERSITY OF PENNSYLVANIA, Philadelphia, PA (US)

(72) Inventors: Duygu Kuzum, Ardmore, PA (US); Ertugrul Cubukcu, Ardmore, PA (US); Brian Litt, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 413 days.

(21) Appl. No.: 15/300,471

(22) PCT Filed: Apr. 3, 2015

(86) PCT No.: PCT/US2015/024229
§ 371 (c)(1),
(2) Date: Sep. 29, 2016

(87) PCT Pub. No.: WO2015/153958
PCT Pub. Date: Oct. 8, 2015

(65) Prior Publication Data
US 2017/0172446 A1 Jun. 22, 2017

Related U.S. Application Data

(60) Provisional application No. 61/974,651, filed on Apr. 3, 2014.

(51) Int. Cl.
*A61B 5/0478* (2006.01)
*A61B 5/04* (2006.01)
(Continued)

(52) U.S. Cl.
CPC ........ *A61B 5/04001* (2013.01); *A61B 5/0042* (2013.01); *A61B 5/0071* (2013.01);
(Continued)

(58) Field of Classification Search
CPC .................................................. A61B 5/04001
(Continued)

(56) References Cited

U.S. PATENT DOCUMENTS 8,751,015 B2 * 6/2014 Frewin ................. A61N 1/0551
607/116
2011/0087126 A1 * 4/2011 Zorzos ................. A61B 5/0478
600/544
(Continued)

FOREIGN PATENT DOCUMENTS

DE 102011112087 * 7/2013

OTHER PUBLICATIONS

Spira, M., "Multi-electrode array technologies for neuroscience and cardiology" Feb. 5, 2013. {retrieved from the internet} {retrieved Jun. 22, 2015},URL:http://www.nature.com/nnano/journal/v8/n2/pdf/nnano.2012.265.pdf.22 ; figure 4 pp. 83-94.
Pashaie, R. "Optogenetics & Brain Interface" Jan. 27, 2013 {retrieved from the internet, on Jun. 21, 2015}. URL:https://pantherfile.uwm.edu/pashaie/www/research.htm>; pp. 3 and 4, figures A-F.
Johnston, H. "Graphene transistors give bioelectronics a boost" Feb. 20, 2013 {retrieved from the internet} {retrieved on Jun. 23, 2015} <URL:http://physicsworld.com/cws/article/news/2013/feb/20/graphene-transistors-give-bioelectronics-a-boost>; p. 1 paragraphs 4-5 2.
(Continued)

*Primary Examiner* — Lee S Cohen
(74) *Attorney, Agent, or Firm* — BakerHostetler

(57) ABSTRACT

A flexible, optically transparent electrode array comprises at least one graph electrode. The electrode may be positioned on a substrate. The flexible, optically transparent electrode may be used for simultaneous optical imaging and electrophysiological monitoring.

11 Claims, 14 Drawing Sheets

(51) Int. Cl.
  *G01N 33/543* (2006.01)
  *C01B 32/182* (2017.01)
  *A61B 5/00* (2006.01)
  *A61N 5/06* (2006.01)

(52) U.S. Cl.
  CPC .......... *A61B 5/0084* (2013.01); *A61B 5/0478* (2013.01); *A61B 5/4839* (2013.01); *A61B 5/6868* (2013.01); *A61N 5/0622* (2013.01); *C01B 32/182* (2017.08); *G01N 33/5438* (2013.01); *A61B 2562/028* (2013.01); *A61B 2562/0209* (2013.01); *A61B 2562/04* (2013.01); *A61B 2562/146* (2013.01); *A61B 2562/164* (2013.01); *C01B 2204/22* (2013.01); *C01P 2006/40* (2013.01)

(58) Field of Classification Search
  USPC .......... 60/373, 377, 383; 600/373, 377, 383
  See application file for complete search history.

(56) References Cited

U.S. PATENT DOCUMENTS

| | | | |
|---|---|---|---|
| 2012/0310071 A1* | 12/2012 | Nakao | A61B 5/0408 600/393 |
| 2013/0090542 A1* | 4/2013 | Kipke | A61B 5/04001 600/377 |
| 2013/0338744 A1 | 12/2013 | Frewin | |

OTHER PUBLICATIONS

International Search Report and Written Opinion for International Application No. PCT/US2015/024229, dated Apr. 3, 2015.
International Preliminary Report on Patentability for International Application No. PCT/US2015/024229, dated Oct. 4, 2016, 6 pages.
Fattahi et al, A Review of Orgainc and Inorganic Biomaterials for Neural Interfaces, Mar. 26, 2014; Adv Mater. Mar. 26, 2014; 26(12): 1846-1885.

* cited by examiner

FIG. 3A
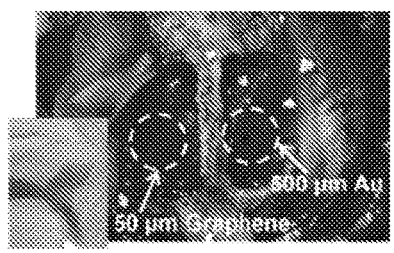
FIG. 3B
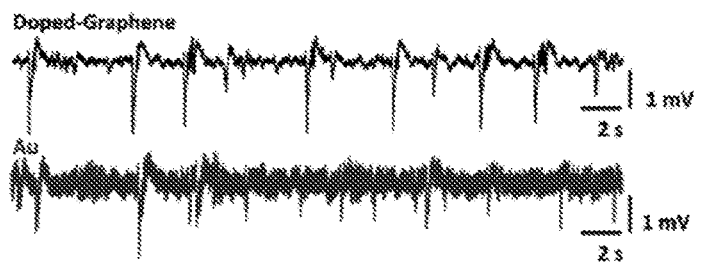
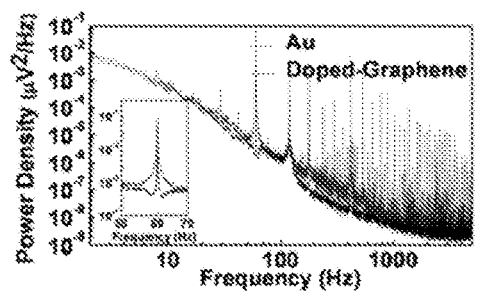
FIG. 3C
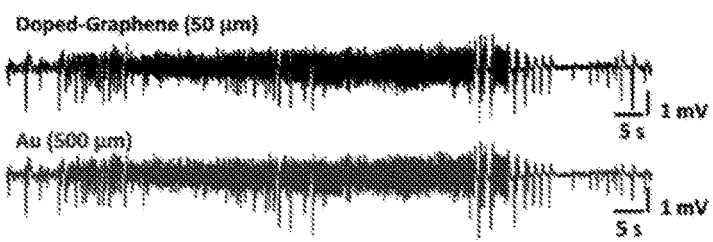
FIG. 3D

FIG. 5A
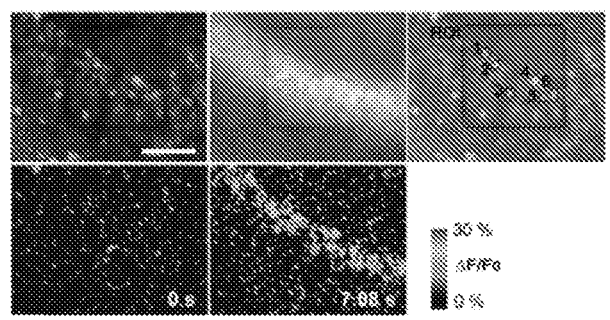
FIG. 5D
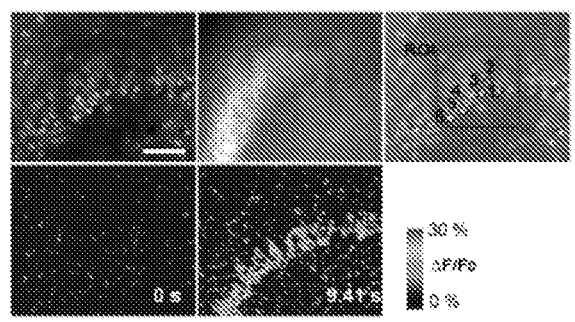
FIG. 5B
FIG. 5E
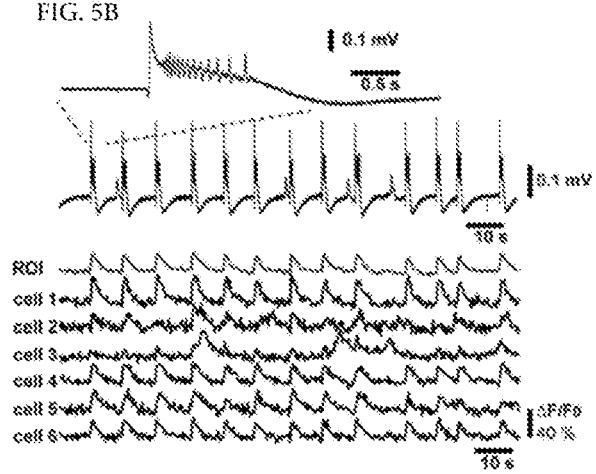
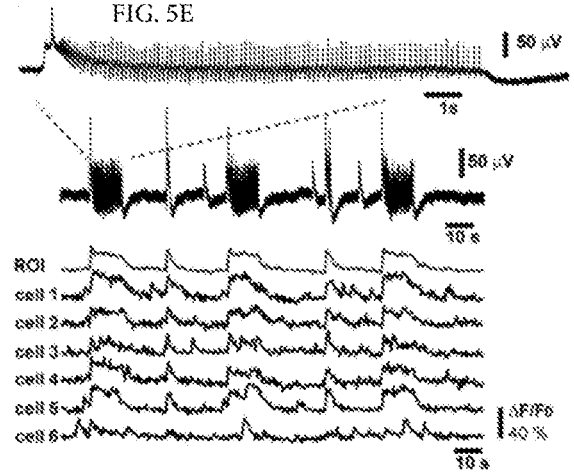
FIG. 5C
FIG. 5F

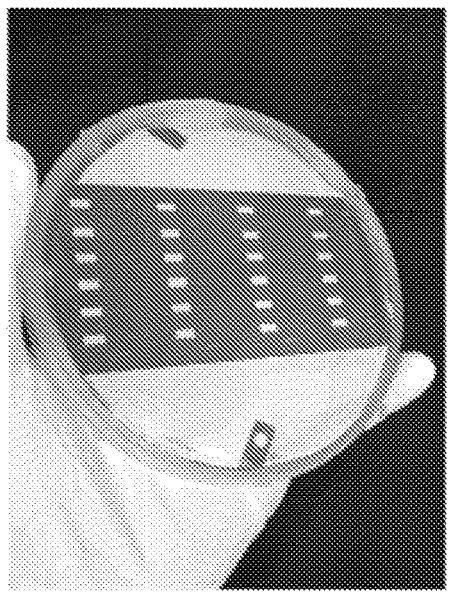
FIG. 7A
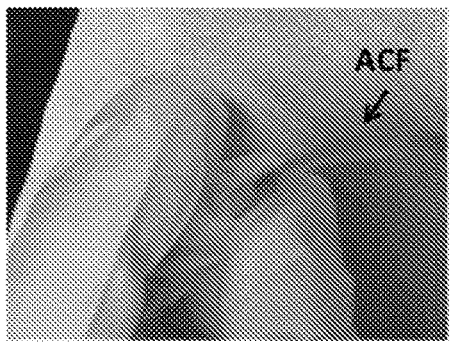
FIG. 7B
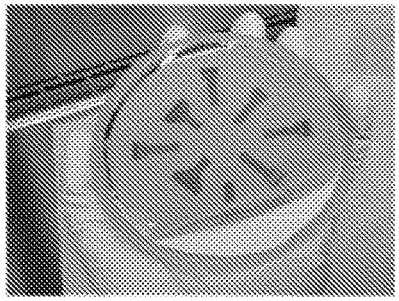
FIG. 7C
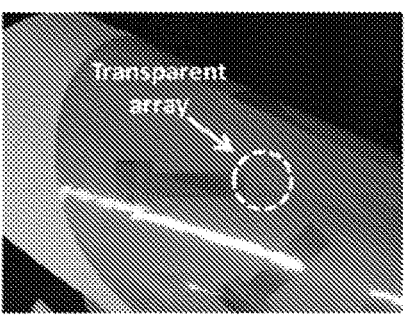
FIG. 7D
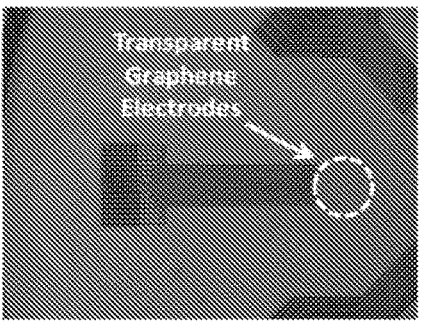

FIG. 8A
FIG. 8B
FIG. 8C
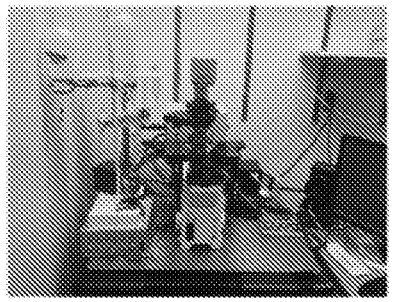
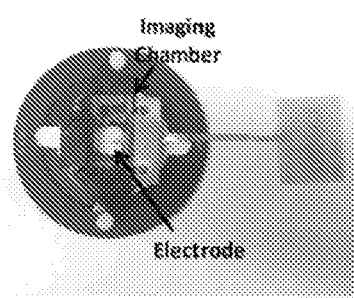
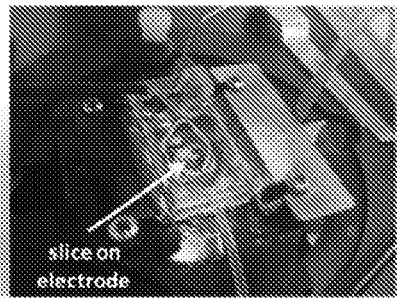

FIG. 15A
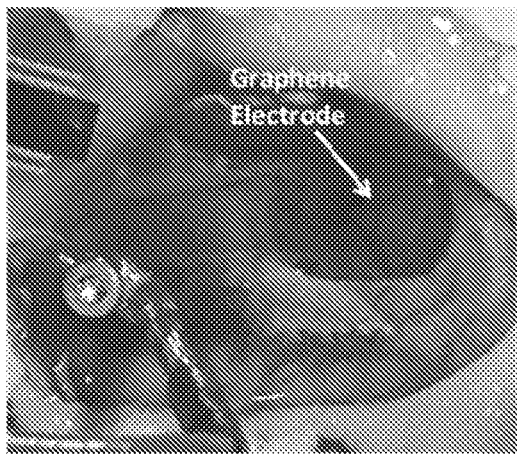
FIG. 15B
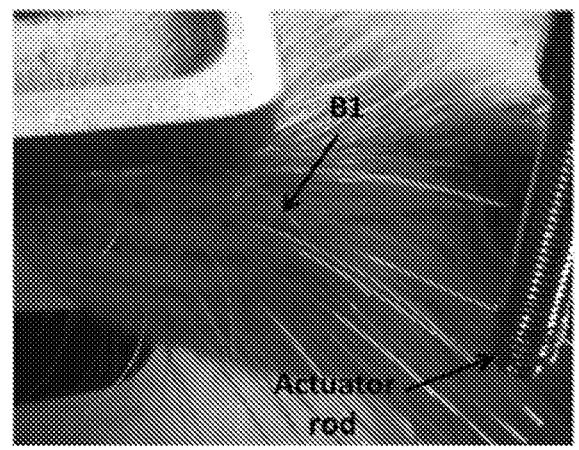
FIG. 15C
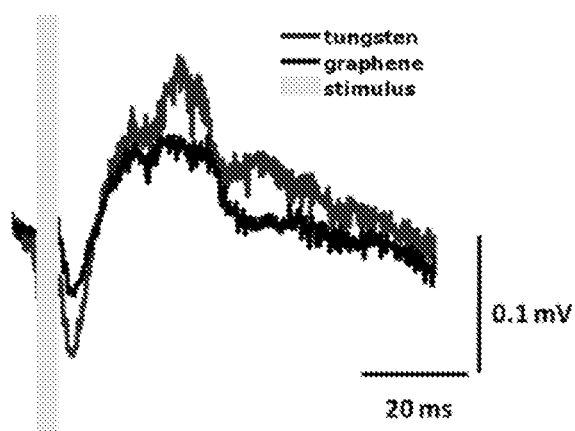
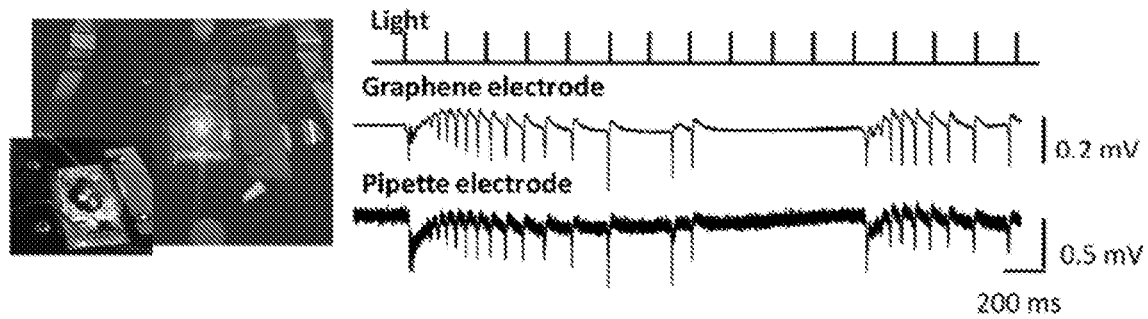
FIG. 16

TRANSPARENT, FLEXIBLE, LOW-NOISE ELECTRODES FOR SIMULTANEOUS ELECTROPHYSIOLOGY AND NEURO-IMAGING

CROSS REFERENCE TO RELATED APPLICATIONS

This application is the U.S. National Phase application of PCT International Application PCT/US2015/024229, filed on Apr. 3, 2015, which claims the benefit of U.S. Provisional Application No. 61/974,651, titled "TRANSPARENT ELECTRODE ARRAYS FOR VISUALIZATION, SIMULTANEOUS IMAGING AND ELECTROPHYSIOLOGY," filed on Apr. 3, 2014, the entirety of which applications are incorporated by reference herein.

FIELD OF THE INVENTION

The present invention relates to transparent, flexible neural electrodes comprising graphene.

BACKGROUND OF THE INVENTION

Calcium imaging is a versatile tool capable of resolving single neurons and their connectivity with single-cell spatial resolution in brain. Unfortunately, its coarse temporal resolution limits its ability to detect neural activity with single spike resolution. Electrophysiological recordings provide high temporal, but limited spatial resolution, due to the dense three-dimensional architecture and geometrical inaccessibility of brain. An approach that integrates the advantages of both techniques could provide new insights into functions of neural circuits.

Studying the complex wiring of neural circuits within human brain is critical for understanding cognitive functions such as perception, learning and memory, and is also vital in developing targeted treatments for neurological and psychiatric disorders. In the past two decades, breakthroughs in neuro-imaging have leveraged our understanding by generating high resolution wiring diagrams of the brain. Functional optical imaging of brain tissue has been shown to provide tremendous information on the dynamic properties of multiple cells (>100) simultaneously. However, fully decoding the functions of individual circuit elements requires simultaneous information on the identity, spatial location and wiring of neurons, as well as their firing patterns, with great precision. Simultaneous electrophysiology and optical imaging could leverage the temporal and spatial resolution advantages of both techniques.

Metal microelectrode arrays commonly used for recording neural activity cannot be used for such purposes, since they block the field of view, generate optical shadows and are prone to producing light-induced artifacts in the recordings. Completely transparent microelectrodes may offer a solution for this spatial-temporal resolution dilemma by enabling simultaneous imaging and electrophysiology from the same microcircuit. In addition, scaling down microelectrode dimensions while maintaining a high enough signal-to-noise ratio (SNR) to faithfully transduce cellular activity has been a major challenge.

Thus, there is a desire for an optically transparent electrode that would allow both visual and electrical detection of neural activity. Transparent electrode technology may pave the way for high spatial and temporal resolution electro-optic mapping of the dynamic neuronal activity, necessary for deciphering mechanisms underlying high-level brain computation.

There have been several attempts to build transparent or partially transparent electrodes, focusing on interfacing neuron cultures grown on rigid substrates or combining them with optogenetic stimulation. Many of those attempts to build transparent electrodes rely on indium tin oxide (ITO). ITO, however, is a very expensive and brittle material, which cracks easily upon bending, making it unsuitable for flexible electrode arrays. Flexibility is particularly important for compatibility with advanced in vivo microscopy techniques in freely behaving animals.

Partially transparent transistors have also been fabricated, however, their opaque source, drain and interconnects make them unsuitable for imaging larger areas or neural circuits.

As of yet, neural recordings with completely transparent, flexible electrode arrays, compatible with in vitro and in vivo imaging techniques, have not been demonstrated.

SUMMARY OF THE INVENTION

One aspect of the present invention relates to a transparent, flexible neural electrode array comprising at least one graphene electrode, which enables simultaneous optical imaging of neural tissue with high signal-to-noise ratio recording of electrophysiological activity.

Another aspect of the present invention relates to a method of simultaneous optical imaging of tissue and electrophysiological monitoring of the tissue.

BRIEF DESCRIPTION OF THE DRAWINGS

FIG. 3. Animal experiment using rat model. (a) The photograph of a 50×50 $\mu m^2$ single graphene electrode placed on the cortical surface of the left hemisphere and a 500×500 $\mu m^2$ single Au electrode placed on the cortical surface of the right hemisphere. The inset shows the flexibility of the electrodes. (b) Interictal-like spiking activity recorded by 50×50 μm² doped-graphene and Au electrodes. Both electrodes were placed on the same hemisphere and connected to the same amplifier channel in subsequent recordings. Data was filtered with a 0.1 Hz-3 kHz bandpass filter. Recordings with doped-graphene electrodes are five to six-fold less noisy compared to the ones with same size Au electrode. (c) Power density spectra of the recordings shown in b calculated over 20 s time window. Doped-graphene electrode recorded significantly lower 60 Hz noise and its harmonics. The inset shows almost two orders of magnitude decrease in 60 Hz electrical interference noise. (d) Seizure-like discharges recorded by 50×50 μm² doped-G and 500×500 μm² Au electrodes simultaneously according to the electrode placement shown in a. Similar SNR are observed for both recordings.

FIG. 5. Multi-cellular calcium imaging and simultaneous electrophysiology recording from the transparent graphene electrode. (a) Left: A steady-state fluorescence (F0) image of the dentate gyrus in a OBG-1 AM stained hippocampal slice obtained by confocal microscopy. The excitation light at 488 nm as well as the fluorescence emission (max at ~520 nm) penetrated through the transparent electrode (graphene and polyimide substrate). Middle: Simultaneously obtained transmittance image. Right: Region of interest (ROI) for electrode area and randomly selected six cells within the electrode area are outlined. Calcium transients from these cells are shown in FIG. 5c. Bottom: Color-coded images of normalized fluorescence change ($\Delta F/F0$) at baseline (0 s) and during one of the peak responses (7.08 s). Scale bar is 50 μm. (b) Recording from the graphene electrode shows interictal-like activity, i.e., short population bursts (shown in insert) that last less than a second, occurring every 5-12 seconds during the 2 minutes of recording. (c) The calcium transient ($\Delta F/F0$) for the electrode area (labeled as ROI) shows an increase in calcium signal coinciding with the interictal-like event recorded in (b). $\Delta F/F0$ traces for individual cells show that most of the cells responded with the interictal-like event but with varied amplitude. Cell 2 did not respond to the third event. Cell 3 only responded to the forth event with a delayed peak. (d) Left: A steady-state fluorescence (F0) image of a different part of the dentate gyrus. Middle: Simultaneously obtained transmittance image. Right: ROI for electrode area and randomly selected six cells within the electrode area are outlined. Bottom: Color-coded images of normalized fluorescence change ($\Delta F/F0$) at baseline (0 s) and during one of the peak responses (9.41 s). Scale bar is 50 μm. (e) Recording from the graphene electrode shows ictal (seizure)-like activity, i.e., prolonged population bursts (shown in insert) that lasted ~10 sec, occurring 3 times during ~150 seconds of recording. (f) Calcium transients ($\Delta F/F0$) for the electrode area (labeled ROI) increased to an elevated level (plateau) with respect to baseline during the ictal-like events. During the ictal-like event, cells 1,2,4, and 5 exhibited plateaus while and cells 3 and, 5 showed multiple peaks. Cell 6 did not participate in ictal-like activity.

FIG. 7. a) Single G, G/Au and Au electrodes, fabricated on polyimide substrate using a 4 inch Si wafer. b) Single G electrode after boding contact pads to flexible ACF cable. Bonding to ACF was performed by applying heat and pressure. c) Transparent ECoG arrays after polyimide peel off from the Si carrier wafer. d) Top: Transparent arrays can wrap around curvilinear surfaces. Bottom: Gold pads and wires connected to completely transparent 16 electrode array. Faded squares are the electrodes.

FIG. 8. a) Confocal microscope setup. b) Insulating chamber built to submerge and constantly perfuse slices placed at the top of the electrode. c) Hippocampal slice placed on the electrode during calcium imaging and neural recording experiments.

FIG. 15. a) 250 µm graphene electrode placed on the surface of the exposed barrel cortex to record the SSEPs produced by vibrissa (whisker) stimulation. b) Left B1 vibrissa was cut to a length of 15 mm and attached to the end of an actuator rod. c) The median of 30 SSEPs recorded with each type of electrode—the grey bar indicates approximate timing and duration of the mechanical stimulus.

FIG. 16. a) Excitation laser illuminated on transparent graphene electrode and hippocampal slice at 5 Hz with a standard glass pipette electrode also placed close to the graphene electrode. b) Recordings by graphene electrode do not exhibit any light induced artifacts.

DETAILED DESCRIPTION OF THE INVENTION

One aspect of the present invention relates to the use of a two-dimensional material, graphene, to build low noise, transparent and flexible neural electrodes for simultaneous optical imaging and electrophysiology. We discovered that graphene electrodes may provide low electronic noise, which may lead to sensor technologies with increased sensitivities, and may enable detection of individual molecules. Graphene may also provide flexibility and protection against corrosion. We also discovered that graphene is optically transparent at wavelengths useful for optical imaging.

Figure 1A:
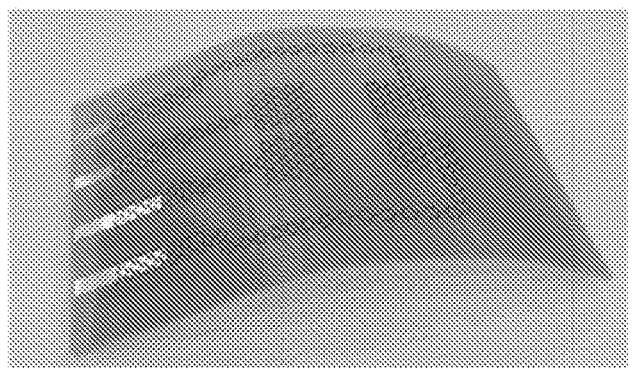
FIG. 1. (a) Schematic illustration of a flexible graphene neural electrode array. Patterned graphene electrodes are in contact with Au contact pads to interface with the data acquisition system. (b) Photograph of a 16-electrode transparent array. The electrode size is 300×300 $\mu m^2$. Inset, a closer view showing the electrode area. Fainted squares are the electrode openings in the encapsulation layer. (c) Microscope image of the array in b. Fainted patterns of graphene electrodes and wires are visible. (d) Microscope image of an 8-electrode hippocampal slice array. The electrode size is 50×50 $\mu m^2$.

Another aspect relates to neural electrode technology based on graphene for simultaneous optical imaging and electrophysiological recording. We developed micro-fabrication techniques to build completely transparent graphene microelectrodes on flexible substrates (FIG. 1a). We have discovered, through electrical characterizations and in vivo neural recording experiments, that graphene electrodes can achieve a significant improvement in signal-to-noise ratio (SNR) and substantial reduction in electrical interference noise compared to gold electrodes. We have also discovered that transparent graphene electrodes can simultaneously record neural activity during calcium imaging with confocal or multi-photon microscopy without any laser-induced artifacts in the recordings. Combination of both techniques revealed temporal and spatial characteristics of high frequency bursting activity and synaptic potentials in hippocampal slices with high precision.

As used herein, the phrase "electrode array" refers to a device comprising at least one electrode. The electrode array may comprise a plurality of electrodes in any arrangement, such as, for example, in rows or lines, or in a grid.

As used herein, the phrase "flexible" refers to the ability of the electrode array to bend and flex. A flexible array is capable of bending without breaking or cracking. According to at least one embodiment, a flexible electrode array is capable of conforming to the surface of the tissue to be analyzed.

The electrode arrays according to the present invention may be flexible and optically transparent. As used herein, the phrase "optically transparent" means that optical measurements or observations may be made through the electrodes on the electrode array using an optical imaging technique. Such optical imaging techniques may include, for example, calcium imaging, voltage sensitive dye imaging, in vivo multi-photon imaging, and optogenetic stimulation. In at least one embodiment, the optical imaging comprises imaging genetically encoded calcium indicators or genetically encoded voltage indicators. On the clinical side, the transparent electrode arrays can be integrated with various brain imaging techniques such as diffuse optical imaging (DOT), event-related optical signal (EROS), and single-photon emission tomography (SPECT). Moreover, because of non-magnetic nature of graphene, it can be integrated with magnetic resonance imaging (MRI), functional magnetic resonance imaging (fMRI), and magnetoencephalography (MEG). Certain optical imaging techniques may require more light to be transmitted than others. In some techniques, however, lower transmission can be at least partially overcome by increasing the stimulus to the observed cells or by using different fluorescent tags.

According to at least one embodiment, the electrode array transmits at least 20% of light at a target wavelength, such as, for example, at least 30%, at least 40%, or at least 50% of light at the target wavelength. In other embodiments, higher transmission may be used, such as 80% or 90% of the light at the target wavelength.

In at least one embodiment, the electrode array is formed on a transparent, flexible substrate. The substrate may comprise a polymer, such as, for example, polyimide, polyethylene terephthalate (PET), polyethylene naphthalate (PEN), or parylene. Other polymers may also be used. According to at least one embodiment, the substrate is flexible enough to allow the electrode array to conform to the underlying tissue. The thickness of the substrate may be selected to provide the desired flexibility or rigidity to the electrode array. For example, when the electrode array is a penetrating electrode array that is implanted, the substrate may be selected based on how the electrode array is implanted. When the substrate provides the rigidity necessary to implant the electrode array in the tissue, the substrate may be selected to have the strength required to implant the electrode array and may be selected from thicker or stronger substrate materials. When the penetrating electrode array is implanted using an implanting aid, such as a microneedle, the substrate may not need as much strength and may be selected from thinner or more flexible materials such that the electrode array may conform better to the surrounding tissue.

Figure 4A:
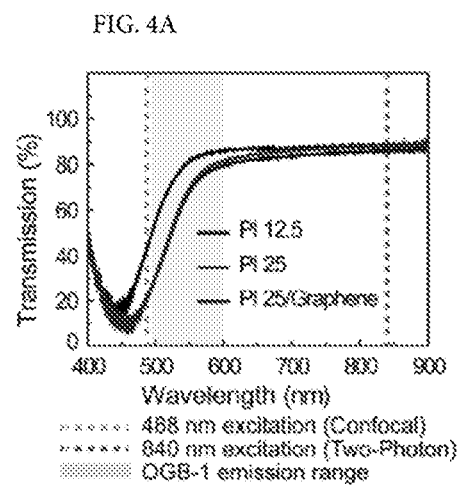
FIG. 4. (a) Optical transmission spectrum of 12.5 μm and 25 μm bare KAPTON® films and 25 μm KAPTON® film coated with graphene. The fluorescence emission range of the calcium indicator dye, Oregon Green Bapta-1 (OGB-1) is shown in green shadow. The excitation wavelength (488 nm) used in the confocal microscopy is delineated by the dotted blue line. The excitation wavelength used in two-photon microscopy (840 nm) is delineated by the dotted red line. (b) Schematic illustration of the confocal microscopy setup with a custom imaging chamber for simultaneous imaging and recording. Insert: Hippocampus slice tissue was mounted on the graphene electrode and perfused with ACSF throughout the experiment. Note that excitation as well as emission light passes through the graphene electrode. (c) Schematic illustration of the two-photon microscopy setup with a custom imaging chamber. Two-photon microscopy operates with an upright microscope equipped with a high numerical aperture water immersion lens. Insert: In order to keep the slice tissue healthy, the custom chamber is equipped with a mesh support and the solution exchange occurs at the bottom of the tissue and the top of the electrode. (d) Left schematic shows different regions of the hippocampus. The dentate gyrus is imaged by the confocal microscope. Images show Left: A steady-state fluorescence (F0) image of dentate gyrus in a OBG-1 AM stained hippocampal slice obtained through the 50×50 μm² graphene electrode. The graphene electrode is seen as a square outline with dark edges. Middle: Simultaneously obtained transmittance image. Right: Merge of the steady-state fluorescence (right) and the transmittance images (left). Scale bar is 50 μm. (e) Dentate gyrus is imaged by the two-photon microscope. Images show Left: A steady-state fluorescence (F0) image of dentate gyrus in a OBG-1 AM stained hippocampal slice obtained through the 50×50 μm² graphene electrode. The graphene electrode is seen as a square outline with dark edges. Middle: Simultaneously obtained transmittance image. Right: Merge of the steady-state fluorescence (right) and the transmittance images (left). Scale bar is 50 μm.

In the examples that follow, electrode array was made using polyimide due to its durability, strength, and chemical and thermal resistance. Other materials may also be used depending on the desired flexibility of the electrode array and the optical transmission properties required for the optical imaging techniques used. For example, as shown in FIG. 4a, an electrode array comprising a 25 µm polyimide and a graphene electrode has a light transmission of about 20% at a wavelength of 488 nm. If a greater light transmission was needed at that wavelength, a thinner substrate or a different substrate material could be used to increase the amount of light transmitted at that wavelength.

According to at least one embodiment, the substrate has a thickness of about 100 µm or less, such as, for example, about 50 µm or less, 25 µm or less, or 15 µm or less. Other substrate thicknesses, greater or smaller, may be used depending on the desired properties of the electrode array.

Figure 11:
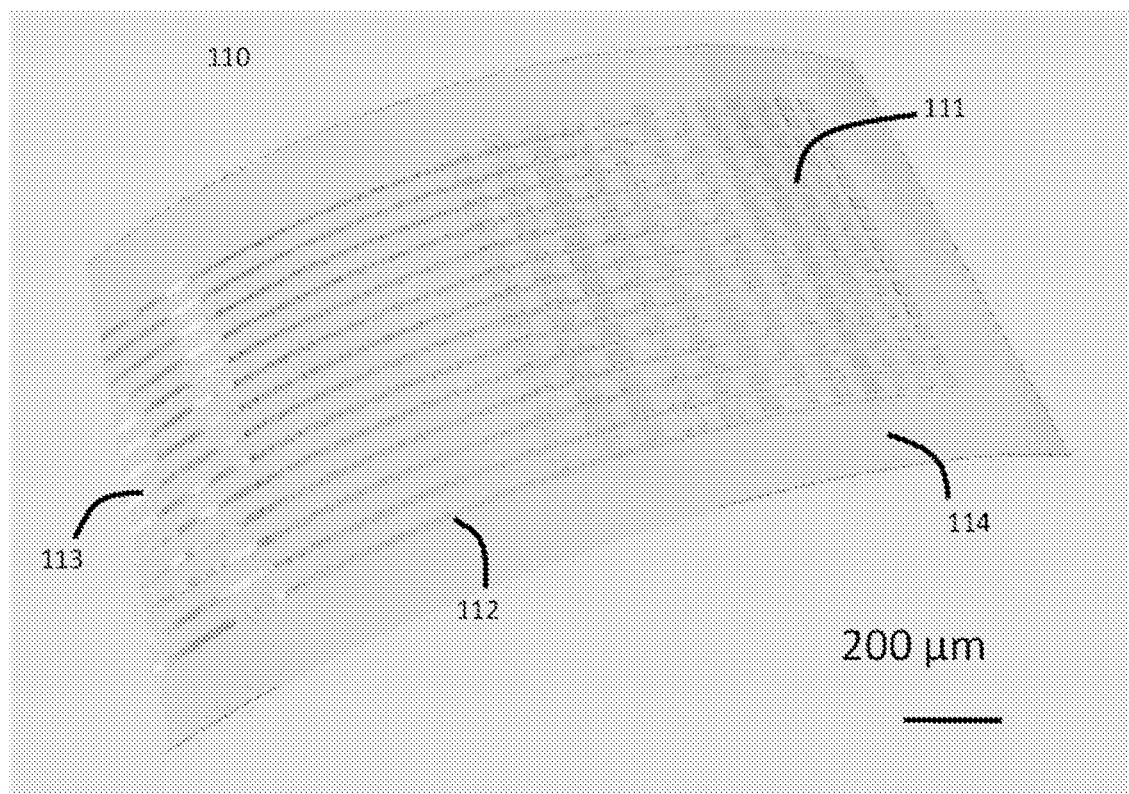
FIG. 11. Transparent flexible surface array for cortical recordings.

In accordance with at least one embodiment of the present disclosure, the electrode array may comprise any known geometry. For example, the electrode array may comprise a flexible surface array for cortical recordings (FIG. 11). The electrode array 110 comprises a plurality of graphene electrodes 111 disposed on a substrate 114 and connected by graphene wires 112. The graphene wires 112 connect the electrodes 111 to gold connectors 113 for connecting to a device. The graphene electrode arrays may be made with varying electrode size, spacing and total number of electrodes based on the design of the electrode. For example, an electrode may have a maximum dimension (i.e., the length of the longest side of the electrode) ranging from less than 10 µm to greater than 500 µm, such as, for example, from 10 to 500 µm. The maximum dimension may be less than 50 µm, less than 30 µm, less than 20 µm, or less than 10 µm depending on the application. The goal of a cortical array is to record local field potentials from the cortical surface at various spatial scales. Small-area arrays, with an area around 1 mm×1 mm and including up to 128 electrodes, may cover the total field of view of the optical microscope used for calcium imaging at 40× magnification. Small-area arrays may focus on interfacing calcium imaging with electrophysiological recordings to study small-scale microcircuits. Electrodes as small as 50 µm×50 µm, overlapping with 5-15 neurons depending on the size and density, may resolve activity of subgroups in the microcircuits. Electrode dimensions can be scaled down to 10 µm, or smaller. Large-area arrays, with up to 256 electrodes with varying dimensions from 50 µm to 250 µm may be fabricated to record from a larger cortex area. Cortical arrays may also include mm-scale holes for inserting penetrating electrodes for recording from the layers beneath the array. The large-area arrays will be used for simultaneous voltage sensitive dye imaging and serial calcium imaging experiments. In serial calcium imaging experiments, at each step, only area under one electrode of the array will be imaged and imaging will be repeated serially at each electrode site.

Figure 12A:
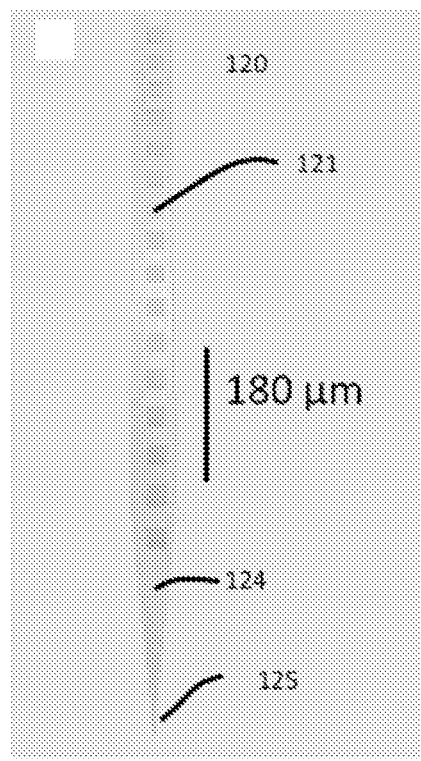
FIG. 12. a) Transparent, flexible minimally-invasive penetrating array for depth recording. b) Penetration of KAPTON® mechanically tested in rat cortex (Penetration depth is ~1.5 mm; thickness of KAPTON® is 50 µm; width at penetrating tip is <50 µm; and width at top is ~100 µm).
Figure 12B:
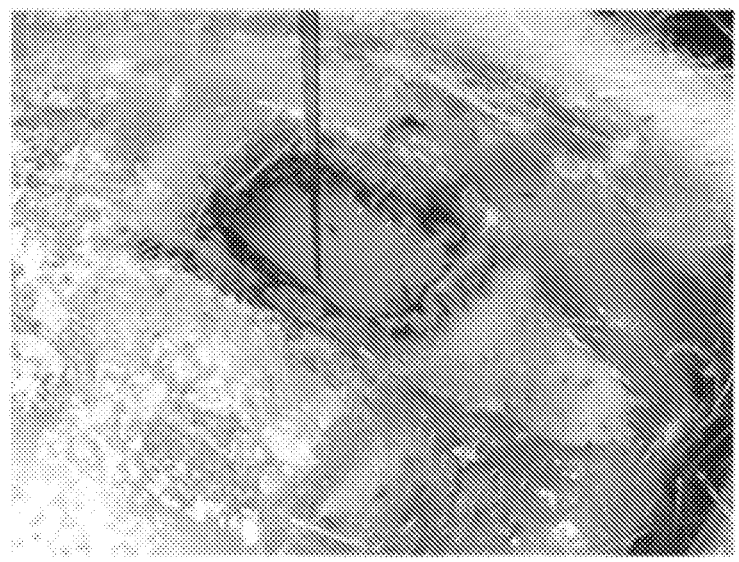
Figure 13:
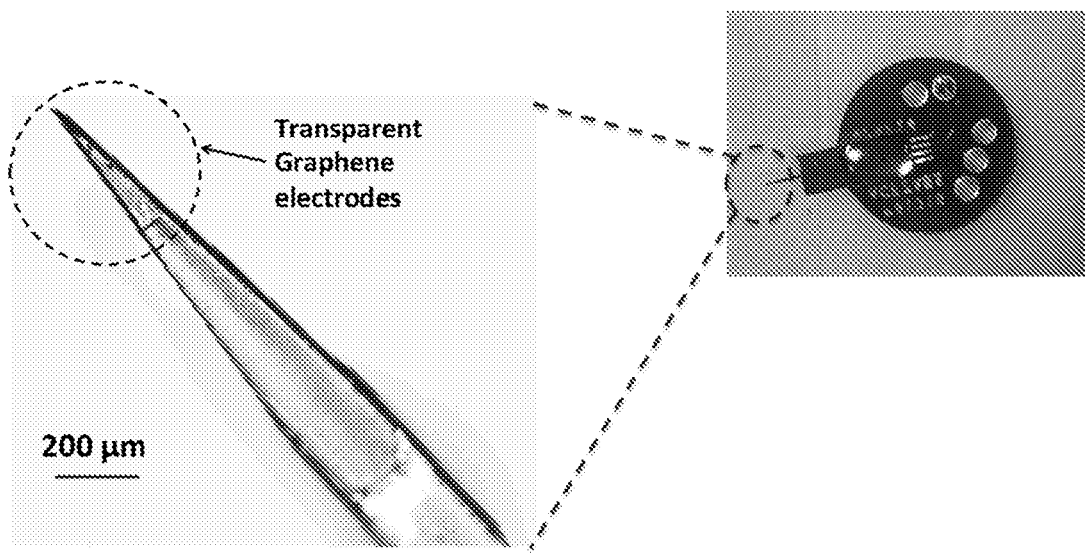
FIG. 13. Transparent penetrating graphene electrode array.

A minimally-invasive penetrating electrode array is shown in FIG. 12a and FIG. 13. In FIG. 12a, electrode array 120 comprises a plurality of graphene electrodes 121 connected by graphene wires (not shown). Electrode array 120 has a substrate 124, which is configured to come to a point 125 for implantation. The goal of a penetrating array is to record single unit and multi-unit activity from deeper cortical layers. The array geometry may be customized depending on the animal model used for probing dynamic cortical circuits. For example, a penetrating array for mice experiments may be 3 mm long, consisting of 16 electrodes with dimensions ranging from 10 µm to 30 µm, and the width of the array may be 200 µm at the top (close to contact pads, not shown) and 30 µm at the tip. FIG. 12b shows a mechanical test of KAPTON® film in a rat cortex having a penetration depth of ~1.5 mm, a thickness of 50 µm, a width at the penetrating tip of <50 µm, and a width close to the top of ~100 µm. Electrical characteristics of 10 µm electrodes may be optimized using dopant engineering and micropatterning to reach desired impedance and SNR values to record single unit activity. Thickness, material characteristics and geometry of the polyimide substrate may be engineered to provide enough stiffness to penetrate in brain tissue. An alternative approach could be using a thin flexible substrate bonded to a stiff carrier microneedle. After penetrating the desired depth, the microneedle can be separated from the flexible substrate and removed from the tissue. This approach may reduce the long term inflammatory response since only the conformable flexible electrode array will be left behind.

According to at least one embodiment, the electrode array and/or the graphene electrode may be functionalized. For example, the electrode array and/or the graphene electrode may comprise a biological molecule, such as, for example, an active pharmaceutical ingredient to improve resistance to inflammation or to aid in the prevention of rejection of the electrode. The biological molecule may be used for neural stimulation. For example, the electrode array and/or electrode may be used to deliver biomolecules for diagnosis or therapy.

The electrode arrays according to the present invention may be encapsulated or coated with an electrically insulating material. The electrically insulating material, for example, may be used to define contact areas of the electrodes and insulate the wires connecting the electrodes to metal contacts, which may be used to connect the electrodes to a measuring or recording device. In at least one embodiment, the electrically insulating material comprises a photoresist, such as, for example, SU-8, a biocompatible, epoxy-based photoresist. Other examples of electrically insulating materials include other polymers, such as parylene C, insulating oxides, such as $Al_2O_3$, SiN, or $SiO_2$, or combinations of polymers and oxides.

Figure 6:
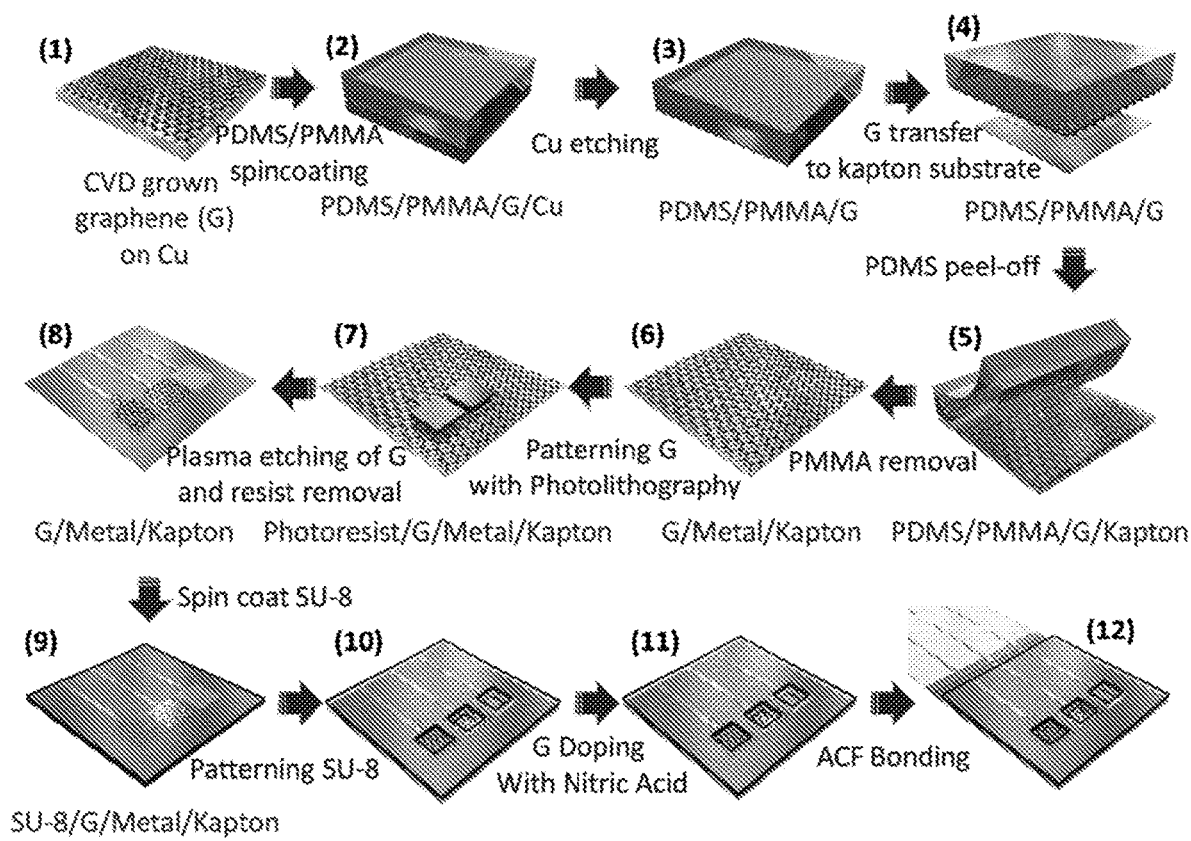
FIG. 6. Schematic illustrating the fabrication process. The fabrication process is shown for three different types of electrodes: graphene (G), graphene/gold (G/Au) and gold (Au).

The electrode array may be fabricated using essentially any known method. One exemplary method is shown in FIG. 6.

In step (1), graphene was grown on a copper foil using chemical vapor deposition (CVD). A transfer layer of poly (methylmethacrylate) (PMMA) backed by poly(dimethylsiloxane) (PDMS) was successively formed by spin-coating the PMMA and PDMS on the graphene-covered copper substrate (step (2)). In step (3), the copper was etched away by selectively etching the copper, leaving the graphene layer attached to the PMMA/PDMS transfer layer.

In step (4), the transfer layer with the graphene layer attached were placed over a KAPTON® (DuPont) polyimide film.

The PDMS layer was peeled away from the PMMA layer in step (5), followed by removal of the PMMA layer in an acetone wash (step (6)), leaving the graphene layer on the KAPTON® film.

A photoresist was spin-coated on the graphene layer, followed by patterning and plasma etching of the exposed graphene (step (7)). The photoresist was then removed to reveal the patterned graphene (step (8)).

The electrode array was spin-coated with SU-8 photoresist (step (9)) and patterned to reveal the electrodes (step (10)).

Selected electrodes were then doped by exposure to nitric acid (step (11)).

An anisotropic conductive film (ACF) was then bound to the formed electrode array for connecting the electrodes to a measuring device (step (12)).

In the fabrication method shown in FIG. 6, PMMA was used to peel the graphene off of the copper film. However, other methods may also be used. For example, Wang et al. ("Direct Delamination of Graphene for High-Performance Plastic Electronics," Small 2014, 10, No. 4, 694-698), hereby incorporated by reference, teaches a method by which graphene can be electrochemically delaminated from a copper film by spin-coating polyimide on the formed graphene layer and using the copper film as a cathode in an electrolytic cell to generate hydrogen bubbles to "push" the graphene away from the copper film. This method may reduce the amount of defects introduced in the graphene layer.

According to at least one embodiment, the electrode array may comprise a single graphene layer, i.e., a single monolayer, or a plurality of stacked graphene layers, i.e., two or more monolayers of graphene.

In accordance with at least one embodiment, the graphene may be doped. Doping the graphene may further decrease the impedance of the graphene. For example, the graphene may be doped with nitric acid to form P-type doped graphene. Other dopants may also be used. In at least one embodiment, the graphene layer is doped by contacting the graphene with nitric acid. The low noise and high electrical conductivity of graphene can provide a promising route for scaling electrode size to single cell dimensions by improving the signal-to-noise ratio, reducing the electrical impedance, and improving charge injection capacity. Furthermore, enhancing the out of plane conductivity of graphene may be very important for electrochemical sensing applications. Chemical doping techniques may reduce the sheet resistance of graphene. By exposing the graphene surface to nitric acid, adsorption of the electropositive $NO_3^-$ groups on the graphene surface results in p-type doping. Electrochemical impedance spectroscopy (EIS) measurements performed on graphene (G), doped-graphene (doped-G) and control gold (Au) electrodes (FIG. 2a) show an improvement by doping. An order of magnitude decrease in electrode impedance with respect to an Au electrode was achieved at low frequencies. The reduction of impedance at low frequencies may have a big impact in suppressing electrical interference noise and electronic noise of the electrode itself.

In embodiments wherein electrode array comprises a plurality of graphene monolayers, one or more of the graphene monolayers may be doped. In at least one embodiment, all of the graphene monolayers may be doped. When forming the graphene layers, the graphene may be doped between the formation of each graphene layer. For example, when the graphene layers are mechanically transferred, the graphene may be exposed to a dopant after each layer is transferred.

According to at least one embodiment, the substrate may be treated to improve the adhesion of the graphene. For example, the substrate may be treated by oxygen plasma etching.

In accordance with at least one embodiment, the graphene may be surface-patterned. Surface-patterning may increase the surface area and electrically active sites of the graphene and improve the impedance. In at least one embodiment, the graphene may be surface-patterned using a photoresist and etchant to create a surface pattern on the graphene.

One aspect of the present invention relates to a method of simultaneously recording electrophysiological activity and optical imaging of neural tissue.

In at least one embodiment, optical imaging and electrophysiological activity monitoring may be used to identify and focus on specific areas. In other words, the use of both techniques may allow for fine-tuning or focusing of the electrode array on areas of interest. For example, the method may enable the identification of small dispersed nerve fibers and allow the electrode array to be focused on specific structures.

Simultaneous optical imaging and monitoring of electrophysiological activity may also allow for the manipulation of the electrode on-the-fly as well as allow the electrode array to be moved to visualize neural activity using both techniques to obtain a greater understanding of the brain function and dysfunction. In this way the array will allow operators to hone in on areas that require foal modulation or therapy.

The electrode arrays can also interface with the central nervous system, peripheral nervous system and other target organs, enabling simultaneous medical imaging and electrical sensing and/or stimulation. The electrode arrays may be included in neural and other tissue electrode cuffs and sheets, in varying geometries, capable of isolating individual electrical sources in tissue, such as activity in much smaller bundles of axons in peripheral nerves, in nerve plexi at the junction of nerves and target organs, such as the innervation to the renal artery, pulmonary musculature, AV or VA nodes in the heart, bladder, bowel, stomach, or other neural controlled or mediated organs or structures. Furthermore, the electrode arrays can be used to sense and control functional networks in the body, neural and other electrically active tissue, and with other functions on the micro-scale.

According to at least one embodiment, a closed loop system can be used to sense and map functional networks using medical imaging while controlling them with electrical stimulation by graphene electrodes. This method can be used, for example, in treatments for chronic pain, epilepsy, depression, movement disorders and other similar "brain-network" disorders. Conversely, the electrode system would allow electrical mapping and modulation, or electrical mapping and modulation with optical techniques, such as optogenetics.

The implantable electrode arrays of the present disclosure may also be used for diagnosis. It is likely that different neurological disorders are marked by specific imaging/electrophysiologic combined signals that may permit their diagnosis or map the severity, extent and location of regions causing these problems, in the operating room. It is also possible that specific disorders, such as types of epilepsy, Parkinson's disease, peripheral nerve, organ, retinal and other disorders may have specific signals that can be diagnosed by combining electrophysiology and imaging. The electrode arrays may be used for diagnostic purposes in the operating room or in the physician's office, such as in the case of the eye. The recording system may also be used in detecting margins between healthy tissue and tissue infiltrated by tumor, based upon simultaneous electrophysiology and imaging studies in vivo. The electrode arrays can also be used to map brain tissue and resection brain tumors.

As noted above, transparent electrode arrays may be useful in performing functional brain mapping over large areas during brain surgery and treatment for cardiac arrhythmias and other disorders. This could be done via surface or penetrating arrays. For example, a transparent electrode array may be placed over the brain, a detailed visual image can then be acquired and an intelligent, functional neurosurgical device may then be programmed to do mapping and ablation or resection, with varying degrees of human control, using combined image and electrophysiologic map of the tissue to steer away from vital tissues, blood vessels, etc., while resecting or lesioning diseased or dysfunctional tissue. Given the flexibility of the electrode arrays of the present disclosure, these procedures may be performed through minimally invasive techniques, including endoscopy.

Examples

Graphene Electrode Fabrication.

Commercial polyimide films (Kapton®, Dupont) with a thickness of 25 μm were attached to a temporary 4 inch Si carrier wafer coated with PDMS, after cleaning it with acetone and isopropyl alcohol. In order to form metal electrodes and contact pads, Cr/Au (10 nm/100 nm) was deposited with thermal and electron-beam evaporation, respectively, on the KAPTON® substrate previously patterned with photolithography. Following liftoff of the metal, CVD grown graphene on Cu substrate was transferred onto the desired areas of the polyimide substrate in contact with the patterned Au pads using PMMA/PDMS stamping method (FIG. 6). The transferred graphene was patterned using photolithography and oxygen plasma etching. Finally, 7 μm SU-8 was deposited and patterned for encapsulation, covering all except the electrode areas. Nitric acid (70%) was used for chemical doping of certain graphene electrodes. As control samples, bare Au electrodes were fabricated in the same batch along with the G and G/Au bilayer electrodes using the same exact process except graphene transfer step. Anisotropic conductive film (ACF) was bonded to the fabricated electrode contact pads to provide electrical connection to data acquisition system through a custom built interface board (FIG. 7).

In Vivo Neural Recordings.

In vivo experiments involved an anaesthetized rat with its head fixed in a stereotaxic apparatus. The animal was anesthetized with ketamine/xylazine throughout the craniotomy and neural recordings. A craniotomy exposed a 4×8 mm region of cortex in both hemispheres. All recordings were taken in reference to a distant stainless steel bone screw inserted through the skull during the surgery. Neural data was acquired by a FHC multi-channel neural amplifier (FHC Inc, Bowdoin, Me., USA) and an acquisition system (16 bit Axon Instruments Digidata 1322A, Axon Instruments, Foster City, Calif.). Recordings were high pass filtered at 0.1 Hz. Neural recording data were analyzed offline using Clampfit software (Axon Instruments).

Figure 14:
FIG. 14. Cortical EEG recorded by graphene electrode in vivo in cat model.

Additional in vivo testing to record cortical spontaneous electro-encephalography (EEG) using a graphene electrode was also carried out in a feline model. The cortical EEG for the feline model in shown in FIG. 14.

Slice Preparation and Staining.

Brains slices were prepared as described previously. Briefly, the brains of male and female rats or mice [postnatal day 2-15 (P2-15)] were removed, glued to an agar block, and sectioned (350 mm) in ice cold artificial cerebrospinal fluid (ACSF) containing the following (in mM): 130 sucrose, 3 KCl, 1.25 $NaHPO_4$, 1 $MgCl_2$, 2 $CaCl_2$, 26 $NaHCO_3$, and 10 glucose. 10 μL of 10% pluonic acid (Lifetechnologies) in DMSO was added to 50 ug of Oregon Green BAPTA-1 AM (Lifetechnologies) and dissolved in 4 mL of ACSF [containing the following (in mM): 130 NaCl, 3 KCl, 1.25 $NaH_2PO_4$, 1 $MgCl_2$, 2 $CaCl_2$, 26 $NaHCO_3$, and 10 glucose] and 4 μL of 5% Cremophor EL (Sigma) in DMSO. The slices were submerged in a chamber equipped with a stirring bar in a water bath with 95% oxygen/5% carbon dioxide, and maintained at 37 C for 30 min. Slices were washed and incubated in oxygenated ACSF at room temperature for at least 30 min before imaging.

Live Slice Imaging.

A slice and an electrode were mounted in custom imaging chambers (modified from commercially available slice recording chambers (Warner Instruments)) and continuously perfused with ACSF or a modified ACSF containing the following (in mM): 130 NaCl, 6 KCl, 1.25 $NaH_2PO_4$, 26 $NaHCO_3$, 0 $MgCl_2$, 2 $CaCl_2$, 10 glucose w/wo 20 μM of 1(S),9(R)-(−)-bicuculline methiodide (Sigma) and continuously bubbled with 95% $O_2$/5% $CO_2$. Slices were imaged on an Olympus Fluoview 1000 Laser Scanning Confocal Microscope equipped with a 20× UPlanApo objective lens (NA=0.70). We focused on a region of area CA3 or dentate gyrus. A time-series movie of fluorescence images was captured, generated by excitation light at 488 nm, eliciting emission between 500 and 600 nm. Transmittance images were captured simultaneously with the fluorescence images. The confocal microscope provided acquisition speed of 2 to 5 Hz with about 250×200 pixel imaged areas. For two-photon microscopy, images were acquired using a Prairie Technologies Ultima multiphoton system attached to an Olympus BX-61 upright microscope. Excitation light was provided by a diode-pumped broadband mode-locked titanium:sapphire femtosecond laser (Spectraphysics MaiTai HP 690-1040, <100 fs, 80 MHz). The laser beam was focused on the specimen by a 40× water-immersion objective (NA 0.90, LUMPlanFL/IR, Olympus). An excitation wavelength of 840 nm was used. Emitted fluorescence was collected with the same objective lens, reflected by a dichroic filter (660LP) passing through in IR cut filter (650SP; Chroma Technology); and detected with a photomultiplier tube (Hamamatsu). Neural recordings with the graphene electrodes were acquired by a CyberAmp 380 neural amplifier and acquisition system (Axon Instruments) with a Ag/AgCl pellet used as a bath electrode. A 60 Hz noise eliminator (HumBug, AutoMate Scientific) was used to reduce electrical line noise interference. Neural recording data were analyzed offline using Clampfit software (Axon Instruments).

Image Analysis.

All images were processed using FIJI or NIH ImageJ software. For calcium transient traces, regions of interest (ROIs) corresponding to somata were selected manually and the average intensity of ROIs was calculated. Custom written Matlab (Mathworks) codes were used to calculate background subtracted normalized fluorescence change ($\Delta F/F_0$). 3×3 median filter was used when generating color-coded $\Delta F/F_0$ movies.

Electrochemical Characterization

Electrochemical impedance spectroscopy, cyclic voltammetry and potentiodynamic polarization measurements were made using Gamry Reference 600 potentiostat/galvanostat/ZRA (Gamry Instruments). EIS measurements were made in standard three electrode configuration and CV was made in two electrode configuration in 0.01 M phosphate buffered saline solution. Impedance measurements were taken between 0.01 Hz and 300 kHz using 10 mV rms AC voltage. For cyclic voltammetry tests the potential on the working electrode was swept three times between −0.8 V and 0.8 V vs Ag/AgCl electrode in PBS solution at a scan rate of 200 mV $s^{−1}$, starting at the open circuit potential. The total charge transfer capability was calculated by taking time integral over the whole CV curve.

To investigate the electrical characteristics of the electrode/electrolyte interface, we used the equivalent circuit model given in FIG. 2d, where $R_S$ is the solution resistance, $C_{PE}$ is a constant phase element representing the double layer capacitor, $R_{CT}$ is faradaic charge transfer resistance and $Z_W$ is a Warburg element for diffusion. Equations for the equivalent circuit elements are listed in Table 1 below. Measured EIS results were fitted to equivalent circuit model to calculate the fit parameters for Au and doped_G electrodes. Porous bounded Warburg element was used to model the diffusion for Au electrode, while bounded Warburg element was used for doped_G electrode because it provided a better fit.

Fabrication and Electrical Characterization of Graphene Electrodes

Figure 1B:
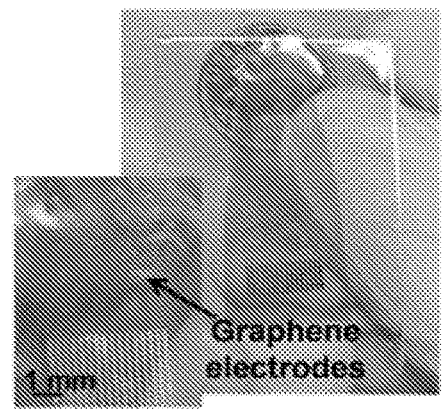
Figure 1C:
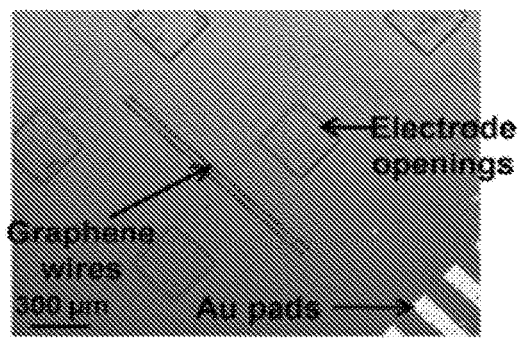
Figure 1D:
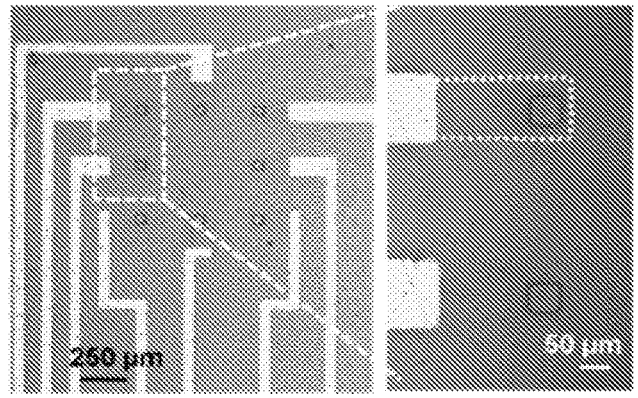

Graphene microelectrodes were fabricated on flexible polyimide (KAPTON®) substrates using a method as shown in FIG. 6. Graphene grown on copper (Cu) by chemical vapor deposition (CVD) was transferred onto polyimide substrate with previously patterned gold (Au) contacts. Following the patterning of graphene, SU-8 was deposited as an encapsulation layer, covering the whole surface except electrode sites. As control samples, bare gold and non-transparent graphene/gold (G/Au) electrodes were fabricated along with the graphene using the same process flow. Graphene samples were doped with nitric acid. Single electrodes were fabricated for electrochemical characterization (FIG. 7a,b). Arrays were designed for in vivo electrocorticography (ECoG) recordings and in vitro hippocampal slice recordings (FIG. 8c,d). FIGS. 1b,c show images of a cortical ECoG array. FIG. 1d shows a microscope image of a hippocampal slice array with 50×50 µm² electrode area. Although graphene provides weak optical contrast, patterning graphene with oxygen plasma etching changes the surface characteristics of polyimide and results in faded patterns, which are slightly visible under optical microscope. The change in surface characteristics does not significantly change the optical properties of the electrode, but may provide a visible guide for determining the location of the electrodes.

The EIS curves for Au and G electrodes had different slopes, implying that the electrochemistry of the electrode interfaces can be different. The phase response of the Au electrode is capacitive (−90°) at low frequencies and becomes more resistive (0°) at higher frequencies. On the other hand, doped-G electrodes exhibit a much more complex phase response, where the phase angle remains constant around −50° for a wide range of frequencies. To better understand the electrochemical characteristics of graphene electrodes, EIS data were fit to an equivalent circuit model (FIG. 2c, Table 1), where the interface is represented by a constant phase element in parallel with a resistor for faradaic charge transfer and a Warburg element for diffusion. Resistance of the phosphate buffered saline (PBS) bath was modeled as a resistor in series with all other elements. The fitting results are plotted in FIG. 2a. The model provides a good fit for impedance results for all three types of electrodes. The phase response results show that the model works for Au and G electrodes at all frequencies. For the doped-G electrode, the model exhibited good fit for the impedance results, whereas some discrepancies between the model and the measurement are observed at higher frequencies for the complex phase response.

TABLE 1

Equations for the equivalent circuit model.

| Equivalent circuit notion | | Equation for impedance | Unit |
|---|---|---|---|
| Solution resistance | $R_S$ | $R_S$ | $\Omega$ |
| Constant phase element | $C_{PE}$ | $\dfrac{1}{Q(j\omega)^n}$ | $S \times s^n$ |
| Charge transfer resistance | $R_{CT}$ | $R_{CT}$ | $\Omega$ |
| Porous bounded Warburg Element | $Z_W$ | $\dfrac{1}{W_0\sqrt{j\omega}}\tanh(B\sqrt{j\omega})$ | $S \times s^{1/2}$ |
| Bounded Warburg Element | $Z_W$ | $\dfrac{1}{W_0\sqrt{j\omega}}\coth(B\sqrt{j\omega})$ | $S \times s^{1/2}$ |

Table 2 below compares the fitting results for the doped-G and Au electrodes quantitatively. The doped-G electrode had a much smaller charge transfer resistance and a more non-linear constant phase element with a much larger constant, representing the capacitive nature of the interface. For neural recording electrodes, having a large interface capacitance helps reducing the electrode noise originating from the resistive charge transfer element. Small charge transfer resistance accompanied with large capacitance for doped-G electrodes could help to suppress electronic noise, which was further investigated by in vivo neural recordings. Cyclic voltammetry (CV) measurements carried out on the same Au, G and doped-G electrodes also verified the improvement in the capacitive characteristics of doped-G electrode. Increased charge storage for doped-G (FIG. 2B) could enhance the amount of transferred charge when graphene electrodes are used for neural stimulation applications.

TABLE 2

Figure 2A:
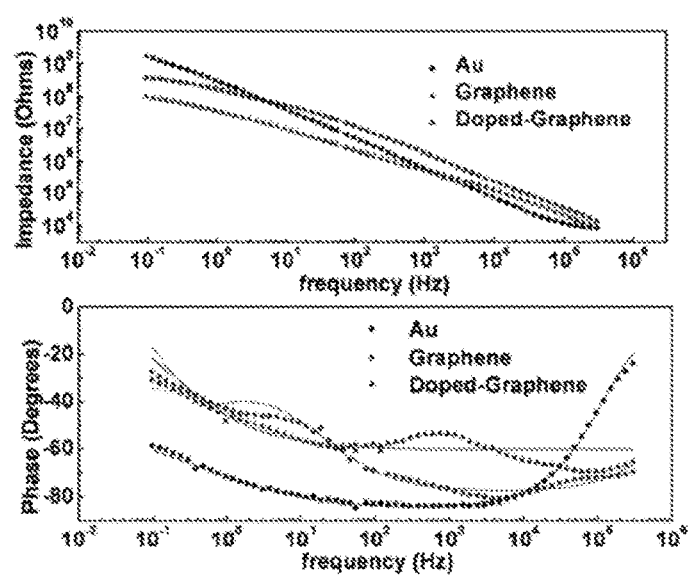
FIG. 2. (a) EIS results for 50×50 $\mu m^2$ Au, G and doped-graphene samples. Measurement results are shown with symbols and fitting results are shown with solid lines for impedance magnitude (top figure) and phase (bottom figure) plots. The impedance magnitude (top figure) significantly decreased with doping of graphene, more prominently for frequencies lower than 1 kHz. (b) Cyclic voltammogram showing enhanced charge storage capacity for doped-graphene electrode. Electrode size is 50×50 $\mu m^2$. Legend shows calculated charge by integrating the area under the CV curve. (c) Schematic for the equivalent circuit model used to fit EIS measurement results. $C_{PE}$ is the constant phase element representing the double-layer capacitance; $R_{CT}$ is the charge transfer resistance; $Z_W$ is the Warburg element representing the diffusion of charges species to the interface; and $R_S$ is the solution resistance. The models for circuit elements are provided in Supplementary Materials.
Figure 2B:
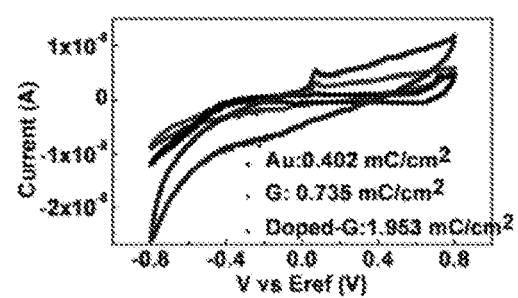
Figure 2C:
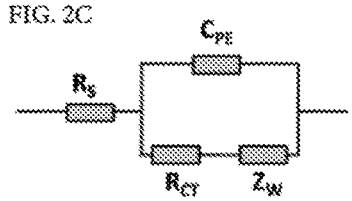

Fitting results for EIS measurements plotted in FIG. 2a.

| | $C_{PE}$ ($S \times s^n$) | | | $Z_W$ ($S \times s^{1/2}$) |
|---|---|---|---|---|
| | Q | n | $R_{CT}$ (M$\Omega$) | $Z_0$ |
| Au | $476.5 \times 10^{-12}$ | 0.94 | 303.0 | $491.4 \times 10^{-12}$ |
| Doped-Graphene | $5.644 \times 10^{-9}$ | 0.67 | 84.9 | $17.36 \times 10^{-9}$ |

In Vivo Neural Recordings with Graphene Electrodes

Lowering the electrode impedance by increasing the effective surface area has been the most standard approach to improve the performance and scale down the sizes of extracellular microelectrodes. However, it is believed that what really determines the electrode performance and its scalability to single-neuron dimensions is the ratio between the recorded neural signal and noise level, i.e., the signal-to-noise ratio (SNR). Impedance and microelectrode area may not be as effective as previously thought in determining electrode performance. This is mainly because the thermal noise associated with the resistive component of electrode impedance is not the only noise source affecting neural recordings. Electronic noise in recording systems, biological noise and other noise sources associated with recording electrodes significantly degrade our ability to detect and sort neural signals.

To better understand the SNR performance of graphene electrodes, in vivo neural recording experiments were performed on an adult rat animal model. In these experiments an anesthetized rat was placed with its head fixed in a stereotaxic apparatus. A craniotomy exposed a 4×8 mm region of cortex in both hemispheres (FIG. 3a). To evoke epileptiform activity, crystals of bicuculline methiodide were applied directly to the recording site before electrode placement. Since the aim of the experiment was to investigate the performance of graphene electrodes, single electrodes of various sizes were used instead of electrode arrays. Graphene electrode and Au control electrodes were placed in the left and right hemispheres to record simultaneously. FIG. 3b shows the low-frequency interictal-like spiking activity recorded by 50×50 µm² doped-G and Au electrodes. Both electrodes were placed on the same hemisphere and connected to the same amplifier channel in subsequent recordings to ascertain that there are no electrode location or amplifier channel-related variations in the measurements. Recordings with doped-G electrodes were found to have five to six times less noise compared to the ones with the Au electrodes of the same size (FIG. 3b), although they have comparable impedance values at around 1 kHz. RMS noise was measured as 30.99±1.15 µV and 165.64±17.87 µV for doped-G and Au electrodes, respectively. The SNR for a given recording was calculated by dividing the signal amplitude by twice the RMS noise voltage (SNR=Signal Amplitude/(2×RMS noise)). Mean SNR was determined to be 40.8 for doped-graphene electrode and 7.7 for Au electrodes in prolonged recordings.

Power density spectra of the recordings with doped-G and Au electrodes calculated over a 20 s time window is shown in FIG. 3c. The doped-G electrode achieved a significant reduction in 60 Hz electrical interference noise and its harmonics. The power of electrical interference noise was reduced approximately 100 times for the doped-G electrode. The suppression of the electrical interference noise for the doped-G electrode may result from the large interface capacitance and small charge transfer resistance found in EIS analysis. This noise suppression suggests a clear advantage for studying brain activity in the low local field potential range (LFP: 1-100 Hz), which includes information on slow synaptic potentials. FIG. 3d shows a sample from experimentally-induced ictal-like activity recorded by 50×50 µm² doped-G and 500×500 µm² Au electrodes simultaneously according to the electrode placement shown in FIG. 3a. Despite a 100-fold difference in electrode area and ~25-fold difference in impedance (at 1 kHz, Au (500 µm): 17.2 kΩ, Doped-G (50 µm): 541 kΩ), the two electrodes showed comparable SNR. These recordings demonstrate the ability of graphene electrodes to record neural activity with high SNR in the LFP band. The capacitive characteristics of the interface may be playing an important role in suppressing intrinsic and extrinsic noise in neural recordings.

Simultaneous Calcium Imaging and Electrical Recording of Neural Activity

Figure 4B:
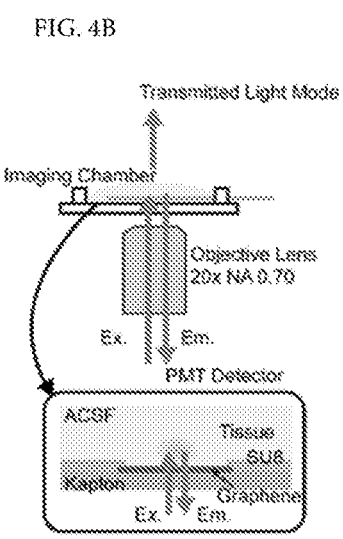
Figure 4C:
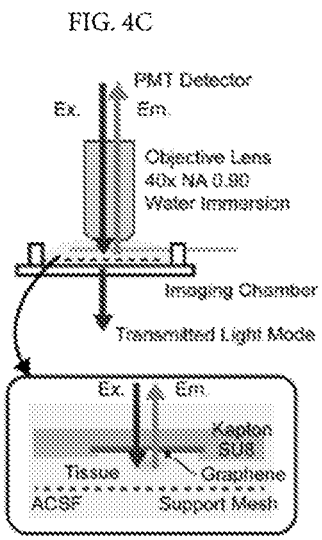
Figure 4D:
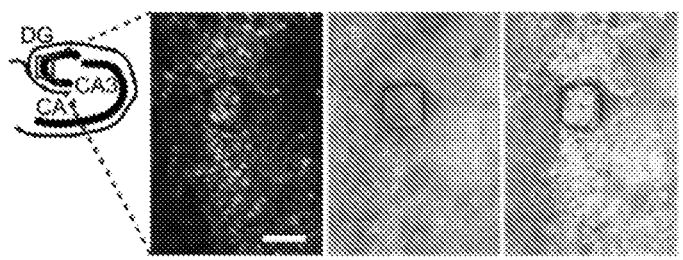
Figure 4E:
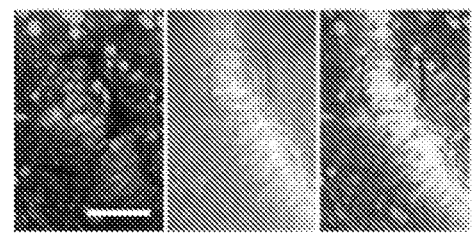

In order to investigate the feasibility of imaging through transparent doped-graphene electrodes, calcium imaging was performed in hippocampal tissue slices by both confocal and two-photon microscopy. First, the transmission spectrum of graphene electrodes fabricated on a polyimide substrate was measured and it was found that the graphene/polyimide was transparent above the wavelength of 450 nm (FIG. 4a). The transmission increases with decreasing substrate thickness and was limited mainly by the polyimide substrate. Calcium indicator dyes such as Oregon Green BAPTA-1 AM (OGB-1) can be used to detect the increase in fluorescence intensity in neuronal cell bodies occurring as a result of calcium influx accompanying action potential firing. For confocal microscopy, OGB-1 is excited at 488 nm (shown in dotted blue line in FIG. 4a) and emits fluoresce between 500 and 600 nm with a peak around 520 nm (shown in green shading in FIG. 4a). For two-photon microscopy, a 840 nm femtosecond laser pulse is used (shown in dotted red line in FIG. 4a) to excite OGB-1. Special imaging chambers were built to submerge and constantly perfuse hippocampal slices and the graphene electrodes in artificial cerebrospinal fluid (ACSF) for the confocal (FIG. 4b and FIG. 8) and two-photon microscopy (FIG. 4c). Hippocampal slices from early postnatal rats (Postnatal day 2-5) were stained with OGB-1, placed on top of a 50×50 µm² graphene electrode in the chamber, and imaged with an inverted confocal microscope. FIG. 4d shows a steady-state fluorescence image of the dentate gyrus (DG) region captured through the graphene electrode. The exposed graphene electrode region, defined by the 50×50 µm² opening in the encapsulation layer, is seen as a square outline with dark edges (FIG. 4d). The excitation light at 488 nm as well as fluorescence emission (max at ~520 nm) penetrated through the 50×50 µm² transparent graphene electrode. Similarly, OGB-1 stained slices from early postnatal rats were placed in the chamber equipped with a support mesh and the graphene electrode was mounted on top of the slice for two-photon imaging on an upright microscope. FIG. 4e shows a steady-state fluorescence image of the DG region imaged through the 50×50 µm² graphene electrode as visualized by two-photon microscopy. Approximately 10 neuronal cell bodies overlapping with the electrode are clearly visible through the transparent graphene electrode.

Electrophysiological recordings were conducted in calcium indicator dye loaded slices to explore the relationship between neuronal activity recordings from graphene electrodes and calcium transients. Potassium ion concentration was elevated to 6 mM (normally 3 mM), magnesium ion concentration was decreased to 0 mM (normally 2 mM), and 20 uM bicuculline-methiodide was added to ACSF to induce spiking activity. FIG. 5a shows a steady-state fluorescence (F0) confocal microscopic image of the dentate gyrus in a hippocampal slice from a P12 mouse stained with the calcium indicator OGB-1. The clear, in focus edges of the exposed electrode region (a square outline with dark edges) indicate that the slice and the electrode are in close proximity. Electrophysiological recordings obtained with the graphene electrode (FIG. 5b) demonstrated interictal-like activity, i.e., short population bursts (insert in FIG. 5b) that lasted less than a second, occurring every 5-12 seconds during the 2 minutes of recording. Calcium transients (LF/F0) within the electrode area (labeled as ROI, FIG. 5c) captured by the confocal microscope show an increase in calcium signal coinciding with the interictal-like event recorded by the graphene electrode. The temporal resolution of the graphene electrode recordings enables detection of high frequency population discharges, which cannot be resolved by the calcium fluorescence responses. In contrast, calcium imaging responses were able to capture complex network contributions of individual neurons which were not evident in the electrical recordings. ΔF/F0 calcium imaging traces for individual cells (FIG. 5c) as well as a snapshot of ΔF/F0 movie (shown in FIG. 5a bottom right) show that most of the cells were activated during the interictal-like event with the amplitude reaching above 30%. Different from other cells, Cell 2 did not respond for the third event and the peak amplitude for each interictal event varied. Cell 3 was not active during most of the interictal-like events except for the fourth event. FIG. 5d-f shows ictal (seizure)-like activity recorded in the same slice. During the ictal-like activity, the calcium transient for the electrode area (labeled as ROI) plateaued at an elevated level (FIG. 5f) with respect to baseline. Simultaneous graphene electrode recordings (FIG. 5e) resolved the ictal-like discharges onset, local field potential, and population bursts. Calcium transients from individual cells exhibited temporal differences in neuronal activity (FIG. 5f). In contrast to the other five cells, Cell 6 had an early response in the first ictal-like event, a late response in the second ictal-like event and late multiple responses during the last event.

Figure 9:
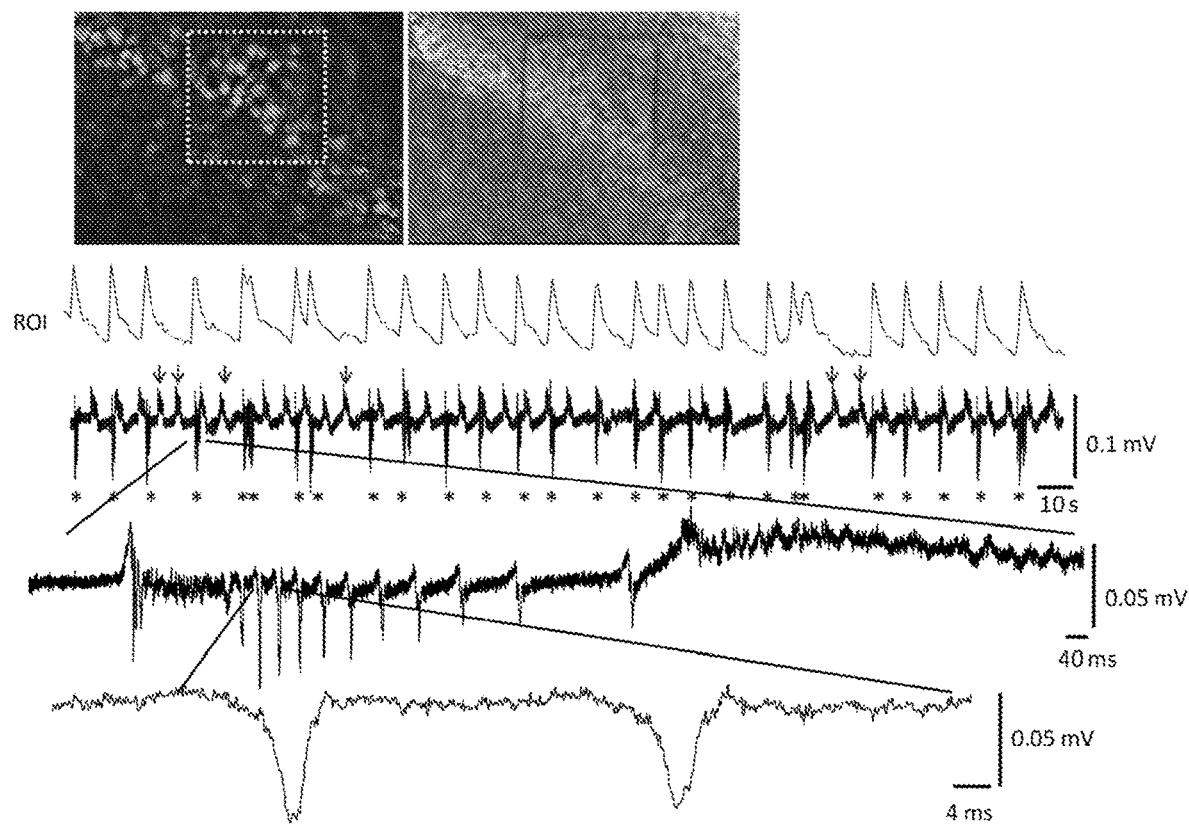
FIG. 9. Multi-cellular calcium imaging and simultaneous electrophysiology recording from the transparent graphene electrode. a) Left: A steady-state fluorescence (F0) image of dentate gyrus obtained by confocal microscopy of a hippocampal slice stained with the calcium indicator OGB-1 AM. The excitation light at 488 nm as well as fluorescence emission (max at ~520 nm) penetrated through the transparent electrode (graphene and polyimide substrate). Right: Simultaneously obtained transmittance image by the confocal microscopy. It clearly shows the edge of the insulating layer, indicating that the slice and the electrode are in close proximity. Calcium transient ($\Delta F/F0$) for the electrode area (labeled as ROI) shows that an increase in calcium signal coincide with the population activity recorded by the graphene electrode. Zoomed traces show that the graphene electrode was able to measure very fast population spikes with durations less than 5 ms. Red arrows show slow synaptic potentials recorded by the graphene electrode. Those were not detectable by multi-cellular calcium imaging.
Figure 10:
FIG. 10. Top trace shows the recordings by graphene electrode and the bottom trace shows recordings by a standard patch pipette placed close to the edge of the graphene electrode. Ictal-like activity recorded simultaneously by the graphene electrode and the patch electrode was found to be consistent.

In another example, the graphene electrode was able to measure very fast population spikes with durations less than 5 ms, as well as slow local field potentials (LFP), which may corresponds to subthreshold synaptic activity. Those LFPs were not detectable by multi-cellular calcium imaging (FIG. 9). For some of the recordings, a standard patch pipette electrode was placed close to the edge of the graphene electrode to record field potentials. Neural activity recorded simultaneously by the graphene electrode and the patch electrode was found to be consistent (FIG. 10). The experiments with hippocampal slices demonstrate that high frequency activity, which cannot be observed by slow calcium transients in calcium imaging, can be detected in simultaneous graphene electrode recordings.

To determine whether graphene electrodes exhibited light induced artifacts, a standard glass pipette electrode was placed close to the graphene electrode (FIG. 16a).

Comparison of the recordings (FIG. 16b) of the graphene electrode and the glass pipette electrode show that the graphene electrodes do not exhibit any light induced artifacts.

Somatosensory-Evoked Potential (SSEP) Experiment

Graphene electrodes were tested in vivo to record somatosensory-evoked potential (SSEP) in anaesthetized rats with no drug application. In the SSEP experiment, two types of working electrodes (standard tungsten electrode and transparent graphene electrode) were sequentially placed on the surface of the exposed barrel cortex to record the SSEP produced by vibrissa stimulation (FIG. 15). The evoked potential measured at the cortical surface by the tungsten and the graphene electrodes consisted of a fast negative waveform followed by a positive long-lasting slow wave, consistently (FIG. 15c). In vivo recordings with graphene electrodes demonstrate their ability to record stimulus-invoked neural activity with high SNR in the LFP band.

Discussion

Our results demonstrate that graphene electrodes in accordance with aspects of the invention enable simultaneous electrophysiological recording and optical imaging, combining the temporal and spatial resolution advantages of both techniques without perturbing either sensing mode. Electrical recordings with the graphene electrode successfully detected interictal and ictal activity, population discharges, and fast population spikes with durations less than 5 ms, which cannot be resolved by multi-cellular calcium imaging. Capturing individual action potentials lasting 0.5-2 ms requires a temporal resolution of at least 0.25 ms. The temporal resolution of the graphene electrode recordings is only limited by the sampling frequency of the data acquisition setup, which is well beyond the requirements to detect action potentials. Spatial resolution can be further increased by scaling electrode dimensions to single-cell size through engineering the charge transfer characteristics and noise of graphene electrodes. The 5-6 fold improvement in SNR and 100 fold reduction in electrical interference noise demonstrated with 50 µm electrodes have already shown graphene's potential to achieve that goal.

We discovered that hippocampal slices can be imaged through transparent graphene electrodes by both confocal and two-photon microscopy without causing any light-induced artifacts in the electrical recordings. Graphene electrodes recorded high frequency bursting activity and slow synaptic potentials in hippocampal slices that could not be resolved by multi-cellular calcium imaging.

In confocal microscopy studies, in order to compensate for the lower transmittance of the polyimide substrate at 488 nm, laser power was adjusted to about four times what is normally used for imaging bright fluorescence samples. For two-photon microscopy, this was not necessary, since the electrodes have high light transmittance at 840 nm. One of the advantages of using two-photon microscopy is the less toxic nature of near-infrared light compared to single photon light irradiation utilized in confocal microscopy. This effect is even more obvious when a UV-excitable dye is used. Selecting a substrate that has higher transmittance above 400 nm would be beneficial when using UV-excitable dyes since their emission usually ranges from 400 to 500 nm or above. Another advantage of two-photon microscopy is its capability to image deeper in the tissue, thus it is often used in in vivo imaging of mouse brains. Combining in vivo two-photon imaging and cortical surface recording by the flexible transparent graphene electrode could present a viable approach to study local field potentials from the cortical surface simultaneously with neural activity from deeper layers. It has been demonstrated that the entire cortical column was imaged in vivo in awake animals using two photon microscopy with a prism implanted in the brain. Incorporation of various optical components and the graphene electrodes might be useful to probe deeper layers and larger areas in the brain tissue.

The techniques developed for single electrodes in this work can be extended to dense arrays in order to study larger areas. A combined sensing and imaging approach capable of simultaneously resolving both synaptic potentials and action potential firing with high spatial and temporal resolution in large populations of neurons could reveal circuit level behavior and correlation between the activities in different parts of brain. Transparent graphene electrodes may be used with optogenetics, enabling optical stimulation of neural tissue. Optical stimulation in combination with multichannel electrophysiology has been a useful tool in assessing network dynamics. However, light stimulation can cause considerable artifact in the recordings due to photoelectric effect in the metal microelectrodes, impeding effective recording of local field potentials. Use of graphene microelectrodes may help to reduce this problem, offering more artifact-free electrophysiology in combination with optical stimulation. Integrating simultaneous optogenetic stimulation, electrophysiological recording, and optical imaging could potentially lead to paradigm shifts in understanding the connectivity and function of neural circuits. Moreover, because of the nonmagnetic nature of graphene, it can be integrated with functional magnetic resonance imaging and other imaging modalities.

We claim:

1. A transparent, flexible neural electrode array device comprising:
    a flexible substrate;
    a plurality of graphene electrodes formed on the flexible substrate; and
    a plurality of wires,
        each wire of the plurality of wires being in electronic communication with a graphene electrode associated with that wire,
        at least some of the plurality of wires comprising graphene, and
        the flexible substrate, electrodes, and the plurality of wires being optically transparent.

2. The device of claim 1, further comprising an electrically insulating material disposed about the flexible substrate, the electrically insulating material defining at least one opening formed therein, the at least one opening being in register with at least one graphene electrode.

3. The device of claim 1, wherein the plurality of graphene electrodes comprises a single monolayer of graphene.

4. The device of claim 1, wherein the plurality of graphene electrodes comprises a plurality of stacked graphene layers.

5. The device of claim 1, wherein at least one of the plurality of graphene electrodes has a maximum dimension ranging from about 10 μm to about 500 μm.

6. The device of claim 1, wherein the at least one of the plurality of graphene electrodes has a maximum dimension of 50 μm.

7. The device of claim 6, wherein the at least one of the plurality of graphene electrodes has a maximum dimension of 30 μm.

8. The device of claim 1, wherein the flexible substrate of the device comprises a pointed tip configured for penetration into a subject.

9. The device of claim 1, wherein the flexible substrate of the device is configured to conform to the surface of a subject's tissue.

10. The device of claim 1, wherein at least one of the plurality of graphene electrodes is functionalized with a biological molecule.

11. The device of claim 10, wherein the biological molecule provides resistance to inflammation or rejection, increases biocompatibility, or provides neural stimulation.

* * * * *

UNITED STATES PATENT AND TRADEMARK OFFICE
CERTIFICATE OF CORRECTION

PATENT NO. : 10,791,946 B2
APPLICATION NO. : 15/300471
DATED : October 6, 2020
INVENTOR(S) : Duygu Kuzum et al.

It is certified that error appears in the above-identified patent and that said Letters Patent is hereby corrected as shown below:

In the Claims

Claim 1, Column 18, Line 52, Replace:
"A transparent, flexible neural electrode array device"
With:
-- A transparent, flexible neural electrode array device, --

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*